United States Patent [19]

West, III et al.

[11] Patent Number: 4,781,871
[45] Date of Patent: * Nov. 1, 1988

[54] HIGH-CONCENTRATION LIPOSOME PROCESSING METHOD

[75] Inventors: Glenn West, III, San Carlos; Francis J. Martin, San Francisco, both of Calif.

[73] Assignee: Liposome Technology, Inc., Dover, Del.

[*] Notice: The portion of the term of this patent subsequent to Jun. 21, 2005 has been disclaimed.

[21] Appl. No.: 909,122

[22] Filed: Sep. 18, 1986

[51] Int. Cl.$^4$ .......................... A61K 9/52; A61K 9/66; A61K 37/22; B01J 13/02

[52] U.S. Cl. ........................ 264/4.3; 264/4.6; 424/1.1; 424/450; 436/829

[58] Field of Search ................. 264/4.3, 4.6; 424/450; 436/829

[56] References Cited

U.S. PATENT DOCUMENTS

| | | | |
|---|---|---|---|
| 4,394,372 | 7/1983 | Taylor | 424/85 |
| 4,508,703 | 4/1985 | Redziniak et al. | 424/450 |
| 4,544,545 | 10/1985 | Ryan et al. | 424/450 X |
| 4,608,211 | 8/1986 | Handjani et al. | 264/4.6 |
| 4,652,257 | 3/1987 | Chang | 604/52 |

FOREIGN PATENT DOCUMENTS 2549736  2/1985  France ................. 210/500.26

OTHER PUBLICATIONS

The Merck Index, published by Merck & Co., Inc., Rahway, N.J., Eighth edition, 1968, p. 875.

Primary Examiner—Richard D. Lovering
Attorney, Agent, or Firm—Ciotti & Murashige, Irell & Manella

[57] ABSTRACT

A method of preparing a concentrated liposome suspension having a lipid concentration of greater than about 250 μm/ml and liposome sizes no greater than about 0.4 microns. A solution of vesicle-forming lipids in a chlorofluorocarbon solvent is injected under selected conditions into an aqueous medium, with continual solvent removal. During the lipid injection and solvent-removal steps, the liposomes formed in the aqueous medium are extruded through a membrane, to reduce liposome sizes to less than about 0.6 microns. The lipid injection, solvent removal, and extrusion steps are continued until a lipid concentration of at least about 150 μm/ml is reached.

14 Claims, 2 Drawing Sheets

HIGH-CONCENTRATION LIPOSOME PROCESSING METHOD

1. FIELD OF THE INVENTION

The present invention relates to methods for preparing liposome suspensions characterized by high encapsulation efficiencies and high lipid concentrations.

2. REFERENCES

Cafiso, D. S., Biochim Biophys Acta 649:129 (1981).
Deamer, D., et al, Biochim Biophys Acta 443:629 (1976).
Gabizon, A., et al, Cancer Research 42:4734 (1982).
Poznansky, M. L., et al, Pharm Revs 36(4):277 (1984).
Schieren, H., et al, Biochim Biophys Acta 542:137 (1978).
Szoka, F. Jr., et al, Proc Nat Acad Sci (USA) 75:4194 (1978).
Szoka, F. Jr., et al, Ann Rev Biophys Bioeng 9:467 (1980).

3. BACKGROUND OF THE INVENTION

Liposomes provide several advantages in drug delivery. When administered parenterally, either by the intravenous or intramuscular route, liposomes can provide controlled "depot" release of encapsulated drug over an extended time period, and reduce the side effects of the drug, by limiting the concentration of free drug in the bloodstream. Liposomes can alter the tissue distribution of and uptake of drugs, in a therapeutically favorable way, and can increase the convenience of therapy, by allowing less frequent drug administration. Liposome drug delivery systems are reviewed in Poznansky.

The use of liposomes for drug delivery by inhalation has also been studied, as reported in co-owned U.S. patent application for "Liposome Inhalation and Method", Ser. No. 737,221, filed May 22, 1985, and now abandoned. The inhalation liposomes can be tailored, according to lipid composition, to release an entrapped drug at a selected release rate which may vary in half life, from a few hours to several days. Further, to the extent the drug is sequestered in the liposomes, side effects related to rapid uptake into the respiratory tract and bloodstream are reduced.

The compatibility of liposomes with both lipophilic and hydrophilic drugs, and the ability to vary lipid composition to achieve a selected drug release rate are also advantageous in administering a drug topically or to mucosal tissue. An added advantage of liposome for drug delivery to mucosal tissue is that the liposome surfaces can be modified for increased tissue stickiness, to enhance the residence time of the liposomes at the target tissue site. This feature is described in co-owned patent application for "Liposomes with Enhanced Retention on Mucosal Tissues", Ser. No. 890,815, filed July 28, 1986.

Several methods for preparing liposomes with entrapped drug are known. In one method, vesicle forming lipids are deposited as a thin film on the sides of a flask, and slowly rehydrated by addition of an aqueous buffer. The drug to be entrapped may be included either in the lipid film (in the case of a lipophilic drug), or in the aqueous hydration medium (in the case of a hydrophilic drug). The liposomes that form are multilamellar vesicles (MLVs) having heterogeneous sizes between about 0.05 and 10 microns.

The MLVs may be subsequently processed, typically by homogenization, sonication, or membrane extrusion, to produce smaller, more uniformly sized suspension. Liposome sizing down to about 0.2–0.4 microns is generally preferred. Liposomes in this size range can be sterilized by passage through a 0.45 micron depth filter, have less tendency to aggregate, and also may show more favorable organ distribution when administered intravenously (Gabizon).

One of the drawbacks of the MLV method is relatively poor encapsulation efficiency of water-soluble drugs. Typically when the vesicles are prepared by addition of an aqueous drug solution, only about 5–15% of the total drug added to the lipid film is encapsulated in the vesicles, Liposome sizing, if needed, reduces the percentage of free drug still more, since liposome sizing methods generally result in some loss of encapsulated material.

Alternative methods for preparing liposomes with higher encapsulation efficiencies have been reported. One of these is a solvent injection, in which a lipid-in-solvent solution is injected into an aqueous medium (Deamer, Schieren, Cafiso). The method produces relatively uniform unilamellar vesicles with encapsulation efficiencies (trapping volumes) of between about 20–45 percent. The higher trapping volumes are presumably related to formation of relatively large unilamellar structures.

Increased encapsulation efficiencies can also be achieved in a reverse evaporation phase method of liposome preparation (Szoka, 1978, 1980). Here a lipid-in-solvent solution is mixed with an aqueous medium, and emulsified to form a water-in-oil emulsion. Removal of the lipid solvent produces a reverse-phase lipid gel which is then agitated, preferably in the presence of added aqueous medium, to form reverse-phase evaporation vesicles (REVs) characterized by relatively large sizes and one to a few bilayer shells. Encapsulation efficiencies for water-soluble compounds are typically between about 30–50 percent of the compound present in the original aqueous medium.

In both the solvent-injection and REV procedures, it may be necessary to reduce liposome sizes, to permit liposome sterilization by filtration and/or to improve the targeting properties of the liposomes. As with MLVs, liposome sizing leads to a loss of encapsulated material.

Since the advantages of liposome drug delivery depend on entrapment of the drug by liposomes, it is generally desirable to administer a drug in predominantly liposome entrapped form, i.e., at least about 50 percent of the drug is associated with the liposomes. This is particularly true where the drug is known to cause undesired side effects when administered in free form. The benefit of administering a water-soluble drug in predominantly liposomal form is illustrated in co-owned patent application for "Liposome Inhalation Method and System", Ser. No. 737,221, filed May 22, 1985, and now abandoned. Here it was shown that the systemic side effects of metaproteranol sulfate (MPS) were substantially reduced when the drug was delivered by inhalation in predominantly liposome-encapsulated form.

In the case of water-soluble drugs, where known liposome preparation methods yield at best 30–50% encapsulation, higher encapsulation levels (above 50% encapsulated drug) can be achieved by treating the liposomes to remove free drug. This can be done, conventionally, by molecular sieve chromatography, centrifugation, or diafiltration. In all of these methods, the bulk phase suspension medium containing the free drug is replaced by drug-free bulk medium.

One drawback of this approach is the additional processing required to remove free drug and, if desired, reclaim the removed drug. A second limitation, in the case of a water-soluble, liposome-permeable drug, is that the liposome composition must be administered before the drug can re-equilibrate between encapsulated and bulk-phase compartments in the suspension. The second problem has been addressed in co-owned patent application for "Liposome Concentrate and Method", Ser. No. 860,528, filed May 5, 1986, and now abandoned. According to this invention, a dilute suspension of liposomes containing a water-soluble, liposome-permeable drug are concentrated to a lipid paste containing at least about 50% and preferably about 70% encapsulated aqueous volume, which also represents the percentage of drug which is encapsulated in the liposomes. The suspension is stored in concentrated form, and diluted shortly before use, i.e., the drug in the diluted suspension is administered in a non-equilibrated, predominantly encapsulated form. The removal of free drug and liposome concentration can be accomplished in a single step by ultrafiltration, centrifugation, or the like. Despite its advantages, the liposome paste approach involves loss of free drug material, and additional processing of the liposome suspension.

4. SUMMARY OF THE INVENTION

It is a general object of the invention to provide a liposome processing method which largely overcomes above-discussed problems and limitations of prior art liposome-preparation methods.

More specifically, it is an object of the invention to provide a method for producing liposomes in which the efficiency of encapsulation of a water-soluble compound is at least about 50% and up to 70% or higher.

Another object of the invention is to provide a method for producing a concentrated liposome suspension which exists in paste- or near-paste form without additional dehydration processing.

A related object is to provide a method for producing such a paste which can be readily sterilized by filter sterilization.

Still another object of the invention is to provide a liposome processing method which can be adapted to produce liposomes in a narrow size range, such as 0.1–0.4 microns, while maintaining encapsulation above 50 percent.

The invention includes, in one aspect, a method of preparing a suspension of liposomes containing a water-soluble compound predominantly—that is, more than 50%—in liposome-encapsulated form. In practicing the method, a solution of vesicle-forming lipids in a chlorofluorocarbon solvent are infused in liquid form into an aqueous medium, under pressure, temperature, and agitation conditions at which lipid frothing is largely prevented, and at an infusion rate that produces predominantly oligolamellar vesicles. The compound to be encapsulated is dissolved either in the aqueous medium or in the lipid solvent. Solvent infusion is continued until the lipid concentration in the aqueous medium is between about about 150–500 $\mu$m/ml. The infused solvent is removed at substantially the same rate that it is introduced, and is removed completely when the selected lipid concentration is reached.

With continued solvent infusion up to a final liposome concentration of at least about 250 $\mu$m/ml, trapping efficiencies of between about 60–70 percent can be achieved. The high-concentration suspension is suitable for use as a liposome paste, e.g., as a storage form for drug-containing liposomes, may be readily converted to a paste by additional water removal, or diluted with drug-free buffer to a desired liposome concentration.

In another aspect, the invention includes a method of preparing a concentrated liposome suspension having a lipid concentration of greater than about 200 $\mu$m/ml and liposome sizes no greater than about 0.6 microns. In this method, a solution of vesicle-forming lipids in a chlorofluorocarbon solvent is infused, as above, into an aqueous medium, under pressure, temperature, and agitation conditions conditions at which lipid frothing is largely prevented, and at an infusion rate that produces predominantly oligolamellar vesicles. The compound to be encapsulated is dissolved either in the aqueous medium or in the chlorofluorocarbon solvent. During the infusing step, the aqueous suspension is circulated through an extrusion device effective to size the liposomes to between 0.1–0.6 microns. Solvent infusion, with continued extrusion and solvent removal, is continued until a final desired liposome concentration—which may be as high as 300–500 $\mu$m/ml—and liposome size range is reached. The concentrated material may be sterilized by filtration through a 45 or 0.22 micron depth filter.

The two methods, when combined, are useful in producing concentrated liposome suspensions (a) having liposome sizes less than about 0.4 microns and (b) water-soluble drug in predomnantly encapsulated form.

In yet another aspect, the liposome suspension is filtered during the solvent infusion and sizing steps, to remove liposomes below a selected size range, and these liposomes are recirculated and mixed with newly infused lipid-in-solvent, during which a portion of the small liposomes are converted to larger ones. By continual filtration, recirculation, and infusion mixing the final liposome suspension can be made substantially free of the smaller liposomes, without sacrificing other advantages of the invention, such as high encapsulation efficiency and high lipid concentration.

These and other objects and features of the invention will become more fully apparent when the following detailed description of the invention is read in conjunction with the accompanying drawings.

DETAILED DESCRIPTION OF THE INVENTION

I. High-Encapsulation Processing

A. Processing System

Figures 1, 2:
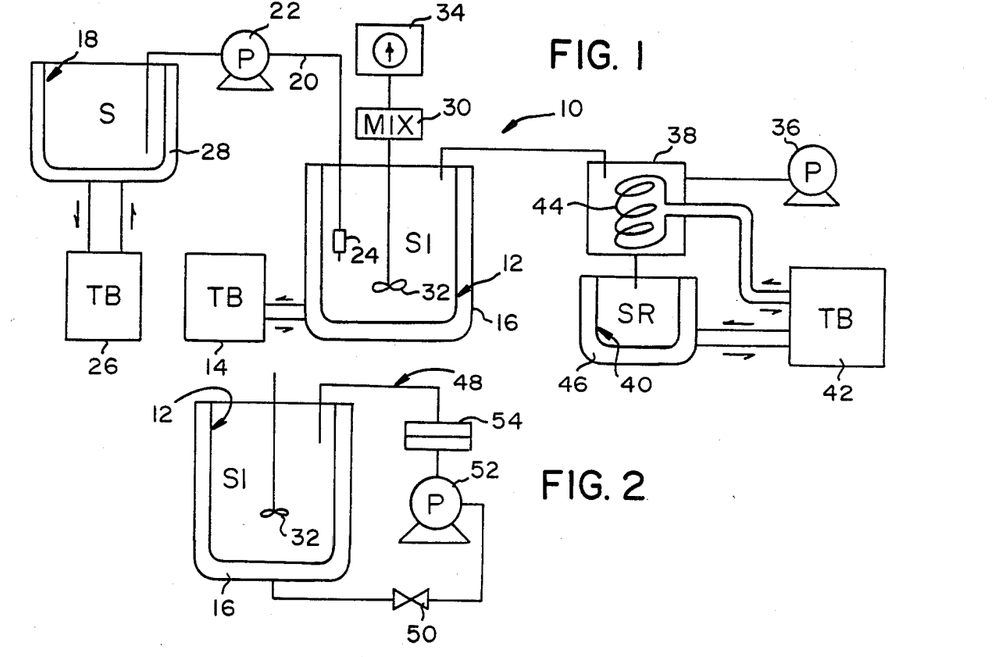
FIG. 1 illustrates in diagrammatic form, a lipid processing system used in practicing the invention.
FIG. 2 illustrates additional components in the FIG. 1 system for use in sizing liposomes by extrusion during liposome preparation.

FIG. 1 shows a processing system, indicated generally at 10, used in preparing liposomes with high encapsulation efficiencies, according to the method of the invention. The system includes a sealed, solvent-infusion chamber 12 which, during operation, contains a given volume of aqueous medium in which the liposomes are formed. The working volume of the chamber may range from 100 ml or less, for small-volume processing, up to 100 liters or more, for scale-up liposome production. The particular system which will be described herein is designed for preparation of up to about 4 liters of liposome suspension in a single batch, and the solvent-infusion chamber has a total volume of about 5 liters. It will be understood that the entire system can be scaled up or down, to accomodate larger chamber volumes.

Chamber 12 is maintained at a constant temperature during operation by a temperature bath 14 which circulates water or other suitable coolant at a desired temperature through a jacket 16 surrounding the chamber. The bath is operable to maintain the temperature of the liquid contents of the chamber above the boiling point of the lipid solvent, and typically at a selected temperature between about 5° C. and 45° C.

The lipid-in-solvent solution is infused into the chamber from a sealed solvent feed tank 18 connected to the chamber through a feeder line 20 and an in-line feed pump 22. The solvent material is introduced into the chamber through a nozzle 24 which is positioned preferably just below the surface of the aqueous medium. Pump 22 is operable to infuse the solvent solution at a rate which is between about 0.5–2 ml, and preferably about 1 ml, per minute per 100 ml aqueous medium in the mixing chamber. Thus if the mixing chambers contains 270 ml of aqueous buffer, the pump is operable to infuse between about 1.4–5.4, and preferably about 2.7 ml solvent per minute into the chamber.

The solvent in the tank and feeder line are maintained at a selected temperature below the solvent boiling point during operation by a temperature bath 26 which circulates a cooled liquid, such as refrigerated water through a jacket 28 surrounding the feed tank and a jacket-like sleeve (not shown) surrounding the feeder line.

A mixer 30 which includes a blade 32 extending into the chamber is used in mixing the liquid contents of the chamber during operation. The blade speed is controlled by a rheostat 34, and is preferably operable produce blade rotation of between about 400 and 1,500 revolutions per minute.

The pressure in the chamber is maintained during operation to a vacuum of about 200 mbar, by a vacuum pump 36. The pump is connected to the chamber, as shown, through a condenser 38 where solvent drawn off by the pump is condensed. The condensed solvent is collected in a solvent-recovery tank 40. A temperature bath 42 supplies cooled liquid, such as refrigerated water, through condensing coils 44 in the condenser, and through a water jacket 46 surrounding tank 40.

B. Processing Components

The lipid-in-solvent solution contains vesicle-forming lipids dissolved in a chlorofluorocarbon solvent whose boiling point is preferably below room temperature, and more preferably, between about 2°–10° C. As defined herein a "chlorofluorocarbon" is a chlorinated, fluorinated carbon or hydrocarbon which has the above boiling point characteristics and which can serve as a lipid solvent. Typical chlorofluorocarbons include "Freon 11" ($CCl_3F$), "Freon 12" ($CCl_2F_2$), "Freon 21" ($CHFCl_2$), "Freon 22" ($CHClF_2$), "Freon 113" ($CCl_2FCClF_2$), "Freon 114" ($CClF_2CClF_2$), and "Freon 115" ($CClF_2CF_3$). A preferred solvent is trichlorofluoromethane ("Freon 11"), whose boiling point is 23.8° C. at 1 atm, or a mixture of trichlorofluoromethane and dichlorofluoromethane ("Freon 21"), whose boiling point is 8.9° C. at 1 atm. Where the compound to be encapsulated cannot be included in the aqueous medium used in forming the suspension, and is not readily soluble in a pure chlorofluorocarbon solvent, the solvent may include up to about 10–20 percent (v/v) of a solvent such as ethanol which is miscible with both the chlorofluorocarbon and water. Minor amount of other organic solvents which are either volatilized under the selected conditions of solvent infusion, or which are tolerated in low concentrations in the aqueous suspension of liposomes may also be included.

The vesicle-forming lipids are selected from known vesicles forming lipids which generally include phospholipids and sterols. A list of phospholipids used commonly in liposome preparation is given on page 471 of Szoka, 1980. Neutral lipid components, such as egg phosphotidylcholine (egg PC), egg pC/cholesterol mixtures may be suitable. However, experiments conducted in support of the present invention indicate that the presence of between about 5–10% charged lipid, such as phosphatidylglycerol (PG), leads to smaller, more uniformly sized liposomes during the coarse of liposome formation. One preferred lipid composition, described in Examples I and II, includes 55 mole percent egg PC, 5 mole percent PG, and 40 mole percent cholesterol.

In addition, the lipid solution may contain lipophilic protective agents, such as α-tocopherol, and/or lipophilic drug compounds which are to be entrapped in the lipid bilayer phase of the liposomes. Representative lipophilic compounds which can be administered in liposome-entrapped form include protaglandins, amphotericin B, progesterone, isosorbide dinatrate, testosterone, nitroglycerin, estradiol, cortisone, dexamethasome and related esters, and betamethasone valerate. As indicated above, the lipid solvent may also contain the water-soluble compound to be encapsulated, where such cannot be included in the aqueous medium used in forming the liposomes. As an example, studies conducted in support of the present invention, and discussed below, show that the water-soluble compound propranolol causes liposome disruption when originally dissolved in the aqueous medium used in the solvent injection method. However, when dissolved in the lipid solvent (Freon 11:ethanol, 10:1), liposomes with very high encapsulated propranolol are formed.

The concentration of lipids in the lipid-in-solvent solution is adjusted to achieve a desired concentration of lipids in the aqueous medium after introduction of a selected volume of the solution. As will be seen below, the minimum concentration of lipids in the final liposome suspension is about 150 μm/ml, and the total volume of lipid solution added to the aqueous medium is between about one-half and twice that of the total volume of aqueous medium in the mixing chamber. Preferably, the lipid solution is made up to between about 200–700 μm/ml. Here it is noted that a mixed chlorofluorocarbon solvent, such as an equal-volume mixture of "Freon 11" and "Freon 21", may be preferred for high-concentration lipid solutions. The concentration of lipids in the solution is adjusted accordingly, so that a desired amount of lipid is added to the aqueous medium, within this volume mixing range.

The aqueous medium is typically a buffered aqueous solution having a pH between about 6.0 and 7.5, and usually containing the water-soluble pharmaceutical agent or compound which is to encapsulated in the liposomes. The pharmaceutical agent may be any drug, hormone, peptide, vitamin, or other pharmaceutical agent which is relatively soluble in the aqueous medium and which can be released from liposomes at a controlled rate, when the liposomes administered parenterally, topically, by inhalation, or other route. The controlled release may be by passage of the agent through the liposomal membrane, in the case of a liposome-permeable agent, or by liposome breakdown, in the case of a liposome-impermeable drug. Representative water-soluble drugs include terbutaline, albuterol, atropine methyl, cromylyn sodium, propranolol, flunoisolide, ibuprofin, gentamycin, tobermycin, pentamidine, penicillin, theophylline, bleomycin, etoposide, captoprel, n-acetyl cycteine, verampimil, fluorouracil, iodouridine, trifluorouridine, vidarabine, azidothymidine, ribavirin, phosphonoformate, phosphonoacetate, acyclovir, cemetidine, naphazoline, lodoxamide, and phenylepinephrine, exemplary of relatively small compounds that may may be diffusable through liposome bilayer membranes. Suitable water-soluble, liposome-impermeable compounds include peptide hormones, enzymes, enzyme inhibitors, apolipoproteins, and higher molecular weight carbohydrates. Representative compounds in this class include calcitonin, atriopeptin, α-1 antitrypsin, interferon, oxytocin, vasopressin, insulin, interleukin-2, superoxide dismutase, tissue plasminogen activator, plasma factor 8, epidermal growth factor, tumor necrosis factor, lung surfactant protein, and lipocortin. The concentration of drug in the aqueous medium is preferably that which is desired in the encapsulated volume in the liposomes.

In addition, the aqueous medium may contain soluble protective agents, such as chelating agents, which reduce oxidative, lipid hydrolysis, or drug degradative effects which may occur on storage.

C. Processing Operation

This section describes the method used in producing liposomes in which the encapsulation efficiency of a water-soluble compound is greater than about 50%, and as high as 65% or more. The operation is described with respect to the processing system and components detailed in Sections IA and IB above. Initially, the lipid solution is added to feed tank 18, and the aqueous medium, to chamber 12, and the two solutions are equilibrated, by temperature baths 26, 14, respectively, to chamber and tank temperatures, above and below the boiling point of the lipid solvent, at the selected pressure. Preferably, where the lipid solvent in "Freon 11", the lipid solvent and aqueous medium are equilibrated to and maintained during operation at about 4° C. and 20° C., respectively.

With the mixer operating a preferred speed of between about 850 revolutions per minute, and the vacuum in the mixing chamber set at between about 200 and 400 mbar, pump 22 is activated to supply the cooled lipid solvent into the aqueous medium contained in the mixing chamber. As noted above, the solvent is infused just below, and preferably between about 1 and 3 cm below the lipid surface in the chamber, and is supplied to the chamber at a preferred rate of about 1 ml per minute per 100 ml aqueous medium. If the infusion rate is too slow, the lipid vesicles which form tend to be more multilamellar in structure, which tends to reduce encapsulation volume per unit lipid. If the infusion rate is too rapid, the lipid material tends to froth, with loss of lipid material and poor encapsulation. Frothing can also be caused by over-rapid removal of solvent vapor from the chamber. Therefore if frothing is observed, and the solvent infusion rate is no greater than that noted above, the vacuum in the system should be reduced until frothing is largely eliminated.

Figure 5A:
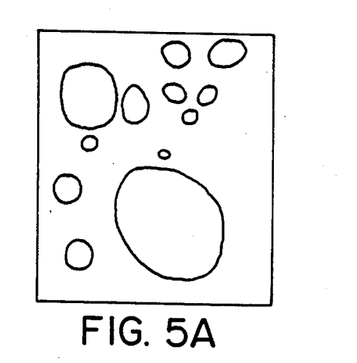
FIGS. 5A–5D are representations of photomicrographs of liposomes taken during a liposome preparation method at lipid concentrations of 50 $\mu$m/ml (4A), 100 $\mu$m/ml (4B), 150 $\mu$m/ml (4C), and 200 $\mu$m/ml (4D).

Under the processing conditions described above, the liposomes formed are largely oligolamellar, i.e., contain predominantly one or only a few bilayers. In the initial phases of the method, the liposomes are heterodisperse in size, ranging from submicron sizes to 10 microns or greater. FIG. 5A shows a typical field of liposomes formed when the total lipid concentration in the mixing chamber has reached 50 μm/ml. The larger liposomes seen in the figure are between about 10–15 microns, and the smaller ones, about 1.5 microns or less. Determination of the percent of encapsulated water-soluble material, according to methods described in Example I, show that the total entrapped volume in the 50 μm/ml preparation is between about 30–35% (Example I).

Figure 4:
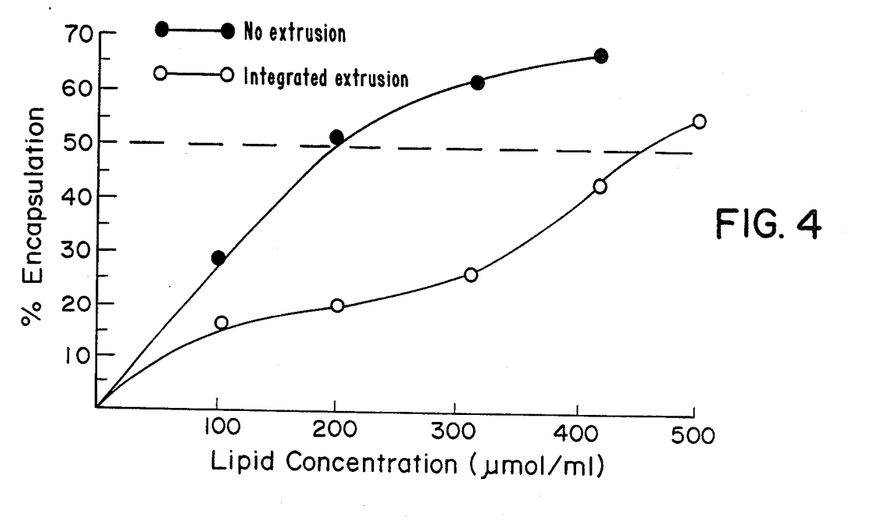
FIG. 4 shows plots of encapsulation efficiency as a function of lipid concentration in two different processing methods carried out according to the invention.
Figure 5B:
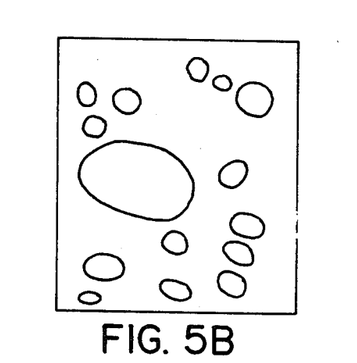
Figure 5C:
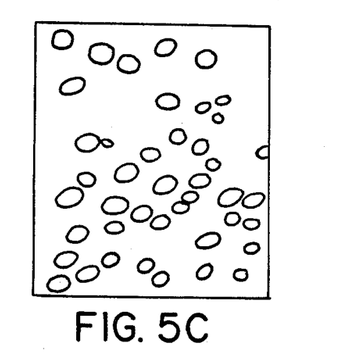
Figure 5D:
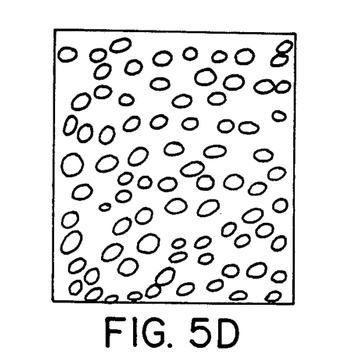

According to an important aspect of the invention, continued addition of lipids into the aqueous suspension results in a continued increase in the percent of encapsulated water-soluble marker (entrapped volume) up to a maximum of between about 60–65 percent encapsulation, at a lipid concentration of about 300 μm/ml or greater. The general increase in encapsulation efficiency, as a function of lipid concentration is seen in FIG. 4. The upper curve (solid circles) in the figure is a plot from one of the processing runs described in Example I. The dotted line in the graph shows the lipid concentration at which 50% encapsulation efficiency is reached. The encapsulated compound is fluorescein, representative of a relatively small, water-soluble compound which is originally contained in the aqueous buffer used in forming the liposome suspension.

Where the vesicle-forming lipids include charged lipid components, such as PG, continued addition of lipid-in-solvent to the mixing chamber produces a gradual size reduction of the larger liposomes in the suspension. This effect is seen in FIGS. 5B–5D, which show the general appearance of the liposome suspension at 100, 150, and 200 μm/ml, respectively. At 100 μm/ml lipid, the general size reduction with respect to the suspension at 50 μm/ml is easily seen, and at 150 μm/ml lipid concentration, almost all of the liposomes are about 1.5 microns or smaller. Further lipid increase to 200 μm/ml did not significantly change the liposome size distribution. Thus, in addition to a high encapsulation efficiency, the method of the invention produces a relatively homogeneous size distribution of liposomes with maximum liposomes sizes less than about 1.5 microns.

It is noted that the gradual decrease in liposome size seen in the method is related to the presence of charged lipid components, and in the case of Example I, to the presence of 5 mole percent phosphatidylglycerol (PG). Examples III and IV below describe solvent unfusion methods involving uncharged lipids, either PC alone or PC and cholesterol. In both examples, final liposome sizes were heterogeneous, and between about 0.1 and 10 microns.

The lipsosome suspension becomes quite viscous at a lipid concentration greater than about 300–400 μm/ml, and further introduction of lipids becomes difficult or impossible. The concentrated suspension has a paste-like consistency which is suitable for several applications which utilize liposome paste material, as will be considered in Section IV below.

The process may be carried out under sterile conditions, using sterile lipid and aqueous components, and by presterilizing the vessels and connective tubing in the system which are in contact with the liquid components. Alternatively, the liposomes may be filter sterilized before in vivo administration. Here the liposomes must be further sized down to maximum sizes of about 0.4 microns. In a preferred sizing method, the liposomes are extruded through a defined pore size membrane, such as a polycarbonate membrane with a 0.4 micron pore size (Szoka, 1982), or an asymmetric ceramic membrane, as described in co-owned U.S. patent application for "Liposome Extrusion Method", Ser. No. 829,710, filed Feb. 28, 1986 and now U.S. Pat. No. 4,737,323, and also discussed below.

Example II describes the polycarbonate membrane extrusion method as it is applied to liposome suspensions having one of a number of lipid concentrations between 100–350 μm/ml. Table 2 in the example shows the encapsulation efficiencies measured for each of the several preparations following extrusion. A comparison of this data with the encapsulation data in Table 1 (Example I) indicates that the extrusion process results in a significant loss of encapsulated material, which is presumably due to larger vesicles breaking and reforming smaller ones during extrusion. The highest encapsulation which can be achieved by the method, at a maximum lipid concentration of about 350 μm/ml, is about 45%. Thus the combined liposome preparation method and subsequent extrusion is limited in lipid concentration to about 350 μm/ml, and encapsulation efficiency to less than 50%. These limitations are overcome in the high-concentration method described below.

Example III describes the use of the present method for producing liposomes with high encapsulation of calcitonin, representative of a water-soluble liposome-impermeable compound which is originally contained in the aqueous medium. The calcitonin liposomes were prepared by infusing a solution of uncharged lipids in "Freon 11" into an aqueous solution of calcitonin, to a final lipid concentration of about 300 μmole/ml. As described in the example, the encapsulation efficiency of the procedure was greater than 60%. Because uncharged lipid components were used, the final liposome sizes ranged up to about 10 microns, as discussed above.

Example IV describes the use of the present method for producing liposomes encapsulated propranolol, representative of a water-soluble which is originally included in the lipid solvent. The propranolol liposomes were prepared by infusing a solution PC and propranolol in "Freon 11":ethanol, 10:1 (v/v) into an aqueous buffer. The presence of ethanol in the lipid solvent was necessary for solubilizing the drug in a chlorofluorocarbon solvent (both "Freon 11" and "Freon 21" were tested). It is also noted that although propranolol is itself soluble in water, attempts to prepare the liposomes by injecting a lipid solution into an aqueous solution of the propranolol were unsuccessful, apparently because of the ability of the propanolol to act as a detergent and disrupt the nascent liposomes being formed during liposome formation.

The infusion process was continued to a final lipid concentration of about 300 μmole/ml, at which about 75% of the drug was encapsulated in the liposomes formed. As in the Example III preparation, which also involved uncharged lipid components, the liposome sizes were heterodisperse, having sizes up to about 10 microns. The ethanol remaining in the liposome suspension after removal of the "Freon" solvent can be removed, if desired, by diafiltration, molecular sieve chromatography or the like. However, the presence of the ethanol in the suspension does not appear to effect liposome stability or reduce encapsulation efficiency.

II. High-Concentration Processing

A. Processing System and Components

The high-concentration method is designed for producing a liposome suspension having (a) a lipid concentration preferably above about 200 μm/ml, and up to about 500 μm/ml and (b) liposome sizes less than about 0.4 microns. The method allows for direct preparation of high concentration liposomes suspension which are readily sterilized by filtration through a 0.45 micron depth filter. When produced in the presence of a water-soluble compound, the liposomes have an encapsulation efficiency of up to 50–60%.

FIG. 2 illustrates a modification of system 10 for use in practicing the high-concentration method. The modified system, which is indicated generally at 48 in FIG. 2, contains all of the components of system 10 which are shown in FIG. 1, including mixing chamber 12, surrounding water-jacket 16, and mixing blade 32 seen in FIG. 2. The system further includes a liposome-extrusion shunt containing a valve 50, a pump 52, and an in-line extrusion device 54. The shunt is preferably designed to circulate suspension in the mixing chamber at a rate which is at least about 5–10% of the total volume in the mixing chamber per minute. That is, the shunt is designed to process the entire suspension volume in the mixing chamber at least every ten-to-twenty minutes. The pump is preferably designed to develop up to several hundred psi pressure, at the volume level just mentioned.

In one embodiment of the system, the extrusion device is a filter device equipped with a 0.2–0.6 micron pore size polycarbonate filter, of the type noted in Section IC. This method is effective to size liposomes approximately to the largest filter pore size, which may be selected from a pore size of 0.1 micron up to 2 micron or larger.

In another embodiment, the extrusion device is an asymmetric ceramic filter of the type constructed of a series of concentric ceramic layers which progress from finer to coarser ceramic mesh on proceeding from an inner to an outer annular space. Filters of this type may be obtained commercially in cartridge from the Norton Co (San Diego, CA), and are available in inner pore (mesh) sizes which are effective in trapping particle size of 0.2, 0.4, or 1.0 microns. The use of this type of filter for efficient liposome sizing has been described in the above-cited U.S. patent application for "Liposome Extrusion Method". According to an important aspect of that invention, it was discovered that liposomes processed in an inside-to-outside direction through a 1 micron ceramic filter were reduced to the desired sizes below about 0.4 microns by only one or a few passes through the membrane.

The ceramic filter device is advantageous in the present invention for the reasons that (a) high extrusion pressures can be used, to achieve higher processing rates, (b) a multiple filter cartridge can handle relatively large volumes in a scale-up operation (c) membrane clogging can be avoided by periodically operating the device in a reverse (outside-to-inside) direction, and (d) the device can be sterilized in place by high temperature or chemical treatment.

The high-concentration processing method uses lipid-in-solvent and aqueous medium components like those used in in the high-encapsulation method described in Section I. The aqueous medium may, but does not necessarily contain a water-soluble pharmaceutical compound for encapsulation in the liposomes. That is, the liposomes may be formulated to contain either a lipophilic compound (which is preferably included in the lipid-in-solvent solution), or an encapsulated water-soluble compound, or both.

B. Processing Operation

The system is operated substantially as described in Section IC. Additionally, when the lipid concentration in the mixing chamber reaches a given concentration, the extrusion shunt is opened, and material in the mixing chamber is circulated through the extrusion device, at a suitable flow rate. Although the shunt may be placed in operation from the time of initial solvent infusion into the chamber, it is generally not necessary to begin extrusion until the lipid concentration in the chamber reaches 50–100 $\mu m/ml$. Below this concentration, vesicles being formed with charged lipid components are becoming progressively smaller as infusion proceeds, as noted above. Above this concentration, liposome extrusion becomes more difficult, requiring higher pressure and producing less efficient sizing due to slower extrusion rates. As indicated above, the shunt is preferably operated at a flow rate which processes the entire volume of the suspension in about 20 minutes or less. More generally, the shunt is operated at a flow rate which allows about 5–10 passes of aqueous volume during the infusion process.

According to an important feature of the method, the integrated liposome sizing step in the method significantly reduces the viscosity of the suspension, at higher lipid concentrations, and this feature allows infusion of additional lipid into the suspension to levels which are substantially higher than those achievable without integrated sizing. As seen in Example V, lipid infusion can be continued up to a final lipid concentration of about 500 $\mu m/ml$, at which the encapsulation efficiency for water-soluble compounds is greater than 50%. Without concurrent sizing, the vesicle suspension would be too viscous to extrude above a lipid concentration of about 300 $\mu m/ml$, even at high extrusion pressure.

Example V illustrates the use of the method for producing a liposome suspension having (a) a final lipid concentration of 500 $\mu m/ml$, (b) liposome sizes less than about 0.2 microns, and (c) an encapsulation efficiency of trapped water-soluble material of about 55%. As in Examples I and II, the suspension was monitored at increasing lipid concentrations to determine encapsulation of a water-soluble marker. The encapsulation data are given in the table in Example V, and plotted (open circles) in FIG. 4. As seen, the extrusion process produces lower encapsulation efficiencies, at comparable lipid concentrations than the system described in Section I. However, because the method allows for higher lipid concentrations, encapsulation efficiencies above 50% can be achieved. As with the preparation described in Section I, greater encapsulation efficiency (for liposome-permeable compounds) can be achieved by additional dehydration, such as described in Section I.

III. Uniform Size Processing

This section describes a system and method for producing a suspension of liposomes which are predominantly in a size range greater than 0.08 microns and preferably between 0.1 and a selected size less than 1.0 microns, e.g., 0.4 microns. The suspension may also be characterized by high encapsulation efficiency and/or high lipid concentration, when the method is combined with one or both of the methods described in Sections I and II above.

A. Processing System

Figure 3:
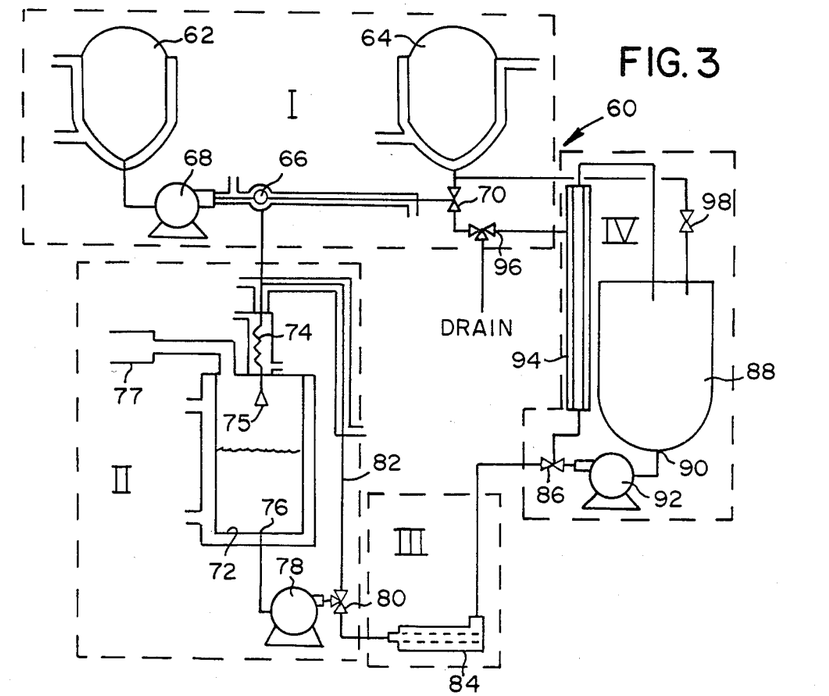
FIG. 3 illustrates portions of an alternate embodiment of a liposome processing system, for use in preparation of liposomes having defined size ranges.

FIG. 3 shows a system 60 desiqned for producing uniform-size liposomes according to this aspect of the invention. For purposes of simplicity, the system will be described with respect to four functional subsystems I–IV which are shown in dotted lines in the figure. These subsystems are designed for (I) mixing buffer and lipid-in-solvent solutions; (II) solvent injection and removal; (III) down-sizing filtration; and (IV) diafiltration and concentration.

The solvent mixing subsystem (I) includes a pair of feed tanks 62, 64 used in supplying a lipid-in-solvent solution and aqueous buffer respectively. Both tanks are pressurized with filtered nitrogen gas to prevent back flow into the tanks and to provide an inert atmosphere within the system. The lipid-in-solvent solution is pumped from tank 62 to a mixing chamber 66 by metering pump 68. Buffer is fed to the mixing chamber under pressure and its flow is regulated by valve 70. The two tanks, the mixing chamber, and the lines connecting the tanks and the chamber are maintained at a temperature below the boiling point of the lipid solvent by suitable tank jackets and tubing heat exchangers, as indicated.

The solvent injection subsystem (II) includes a heat jacketed vacuum chamber 72 which is connected to the mixing chamber through a heat-jacketed static mixer 74. The mixer functions to mix the lipid/and buffer solutions as they pass from the mixing chamber into the vacuum chamber, and delivers the mixed material into the chamber as a fine spray through a spray nozzle 75. As will be seen, a heated fluid circulating through the mixer jacket serves to warm the solvent/buffer mixture in the mixer above the boiling point of the solvent before injection into the vacuum chamber. The vacuum chamber is evacuated to a selected pressure by a vacuum source 77.

Chamber 72 communicates through a drain 76 with a high-pressure pump 78 which functions to continuously recirculate fluid contained within the chamber through a closed loop containing a three-way flow regulating valve 80, a conduit 82 and mixer 74. As seen, conduit 82 supplies material into the mixer downstream of the mixing chamber. The downstream end region of the conduit is heat jacketed, to cool the material being supplied to the mixer below the boiling point of the lipid solvent.

The down-sizing subsystem (III) includes a filter 84, such as a polycarbonate or ceramic filter of the type described above, which is effective to reduce liposome sizes to a selecteo size range, preferably below about 1-2 microns. Material is fed into the filter from valve 80, which can be adjusted to divert a portion of the liquid from the vacuum chamber through the filter. The downstream end of the filter communicates through a valve 86 with the fourth subsystem, which will now be described.

The fourth subsystem is composed of a holding tank 88 equipped with a bottom drain 90 which is connected to the intake of a pump 92 which serves to circulate the fluid contained in the holding tank through diafiltration filter 94. The diafiltration filter pore size is preferably selected to retain liposomes larger than about 0.2 microns. The retentate from the diafiltration filter (larger liposomes) is returned to the holding tank and the filtrate passes through a three-way valve 96 which either diverts the filtrate (smaller liposomes) to drain in the case of concentration operations or to the three way flow regulating valve 70 for diafiltration and up-sizing operations. During these latter operations, the filtrate is fed to mixing chamber 66 by adjusting valve 70. Completing the description of the fourth subsystem, buffer may be supplied directly from tank 64 to tank 88 through a valve 98.

B. Operation of the System

Operation of the system can be divided into five phases: (1) start-up, (2) injection/solvent removal, (3) down-sizing, (4) diafiltration/up-sizing, and (5) diafiltration and concentration.

During the start up of the system, the lipid-in-solvent solution is held in its feed tank while aqueous buffer is allowed to pass from tank 64 into vacuum chamber 72, until the chamber is about half full. The chamber is heated by its external heat jacket until the buffer in the chamber is above the boiling temperature of the lipid solvent. The pressure in the chamber is lowered by vacuum source 77. The heated buffer contained in chamber 66 is then circulated by pump 78 through conduit 82 and mixer 74 and back into chamber 72. During start up, valve 80 is set to direct the entire flow from pump 78 through conduit 82, but as described below, during the down-sizing and diafiltration/up-sizing phases of operation the valve is set to meter a portion of the loop flow through a sizing filter and into the diafiltration loop circulation.

As the heated buffer circulates through conduit 82, it is cooled by the heat exchanger in the conduit below the boiling point of the lipid solvent. Before reentering the vacuum chamber, the recirculated buffer passes through the static mixer which here serves two purposes: it provides thorough mixing of the lipid-in-solvent/buffer mixture with the fluid recirculating through the loop (during the injection/solvent removal phase) and it heats the mixture to a temperature above the boiling point of the lipid solvent (which facilitates solvent removal in the vacuum chamber). The start up phase ends as temperatures of the fluids and pressures within the vacuum chamber and process lines equilibrate at the appropriate values.

During the second, solvent-injection phase of operation, liposomes are produced as the lipid solvent is removed from the lipid-in-solvent/buffer mixture. Here the lipid-in-solvent solution in tank 62 is introduced into chamber 66 by the metering pump 68, and aqueous buffer held in tank 64 is fed into the mixing chamber under pressure. The two solution mix in mixing chamber 66 and the lipid-in-solvent/buffer mixture is subsequently mixed with the aqueous buffer being recirculated through the solvent removal subsystem immediately upstream of static mixer. Importantly, at the point of mixing, all solutions are at a temperature below the boiling point of the lipid solvent. As the mixture passes through the static mixer the temperature is raised to a point above the boiling point of the lipid solvent (at the pressure set in the vacuum chamber). Following passage through the static mixer, the mixture is sprayed into the vacuum chamber as a fine mist by nozzle 75. Since the lipid solvent will vaporize at the temperature and pressure present in the chamber, the bulk of the solvent is stripped from the mixture as the droplets fall through the chamber. The vaporized solvent is condensed by a condenser (not shown) connected to the vacuum system. The lipid which is left behind as the solvent is removed, forming liposomes ranging in size between about 0.1 to 20 microns in diameter. The lipid-in-solvent/buffer mixture injection coupled with solvent removal continues until the lipid concentration in the aqueous phase reaches the desired level, whereupon valve 80 is adjusted to divert a fraction of the fluid supplied from pump 78 to the down-sizing filter subsystem. A balance is struck so that the same volume of buffer entering through the injection system is diverted to the down-sizing filter subsystem.

During the third, down-sizing phase of operation, the liposomes formed during the injection phase in the vacuum chamber are sized by passage (extrusion) through filter 84. Following extrusion, the suspension of reduced-size liposomes is combined with the fluid circulating through the diafiltration system by adjusting valve 86.

In the diafiltration/up-sizing phase of operation, liposomes smaller than the pore size of the diafiltration filter, e.g., 0.1 micron, enter the filtrate and are delivered to the mixing chamber following passage through valve 96 and valve 70. Once in the mixing chamber, the filtrate is exposed to the lipid-in-solvent solution being introduced from tank 62. The solvent content in the mixing chamber is sufficient to extract the lipid from the small liposomes present in the filtrate. This lipid is combined with the lipid entering in the lipid-in-solvent solution and is injected into the lipid-in-solvent/buffer injection and solvent removal subsystem for formation into new liposomes. During this phase of the operation fresh buffer may be introduced from tank 64 into the filtrate material, to offset the loss of volume in the retentate from the diafiltration filter, or, alternatively, by not adding additional buffer to the filtrate, the system can be operated in a mode which concentrates the liposome suspension during operation.

In the final diafiltration phase of operation, valve 96 is adjusted to divert the filtrate from the diafiltration filter to a drain and valve 98 is adjusted to deliver the same volume of fresh buffer to tank 88 as is being removed by diafiltration. The final concentration phase of operation follows the procedure used during diafiltration, with the exception that valve 98 is closed so that no fresh buffer is added. The product in tank 88 becomes progressively more concentrated as filtrate is removed by the diafiltration cartridge. The process is terminated when the liposome suspension reaches the desired concentration.

IV. Utility

A. Liposome Diagnostic Reagents

One liposome-based diagnostic test is based on complement-mediated liposome lysis, in response to the presence or absence of an analyte of interest. The liposomes used in the test contain a surface bound ligand which is designed to bind to or compete with the analyte of interest, and an encapsulated reporter, such as a fluorophore, chromophore, or enzyme, whose release from the lysed liposomes can be quantitated to determine the concentration of analyte in the reaction sample.

The methods described herein provide two important advantages in the preparation of liposomes suitable for this type of assay. First, the liposomes formed are predominantly uni- and oligolamellar, and are therefore are more sensitive to lysis than multilamellar liposomes. Secondly, particularly where the encapsulated reporter is an enzyme, the liposomes can be formed with little loss of enzyme, under conditions which are generally non-disruptive of enzyme activity.

B. Parenteral Drug Administration

Liposomes having sizes less than about 0.4 microns and and predominance of liposome-entrapped drug are ideally suited for parenteral administration of the drug, either by intravenous or intramuscular route. The present invention provides a simple, efficient method for preparing liposome suspensions of this type. In particular, encapsulation rates of up to about 75%, in the case of unsized liposomes, and up to about 55%, in the case of concurrently sized liposomes, for a water-soluble compound can be achieved without additional sizing and dehydration processing. The high encapsulation efficiency is especially advantageous in forming liposomes with encapsulated peptides or hormones, since the total amount of non-encapsulated material is relatively small, thus avoiding or reducing compound-recovery problems.

The ability to produce sized liposomes at high concentration may be an added advantage in some parenteral uses. An example is the use of liposomes for controlled drug releasd from an intramuscular site, as reported in co-owned U.S. patent application for "Controlled-Release Liposome Delivery System", Ser. No. 828,153, filed 2/10/86. The system is based in part the discovery that release of encapsulated drug from administered liposomes can be increased in a controlled manner by increasing the amount of liposome lipid injected into the site. It can be appreciated that the high concentration formulations produce by the present invention have the potential for greater release times than prior art formulations.

C. Liposome Inhalation

The use of liposome pastes and high-encapsulation suspensions for drug administration by the inhalation route high been described in the above-noted U.S. patent application for "Liposome Inhalation Method and System". Briefly, paste formulations provide a ideal storage form for liposomes where the entrapped drug is water-soluble and liposome-permeable, e.g., where drug equilibration of the drug between encapsulated and bulk aqueous compartments occurs. The present invention provides a simple means for forming such a paste directly, or with little additional water removal. For drug administration, the paste is diluted, preferably to between about 10-30 volume percent, and the diluted suspension is atomized in a form suitable for inhalation, before significant drug equilibration can occur.

Alternatively, the liposomes can be administered in dry, particulized form, also as detailed in the above-cited co-owned patent application. Here, the liposomes are prepared in the presence of a bulking agent, such as mannitol, sorbitol, or the like, dried by dehydration, and particulized, for example, by grinding. The particles can be atomized in powdered form or suspended in a chlorofluorocarbon solvent for atomization. The advantages of the high-encapsulation method in this application are (1) reduced dehydration time (2) less damage to the liposomes on freezing, prior to lyophilization, and (3) higher encapsulation of water-soluble material.

D. Topical and Ophthalmic Uses

The liposome paste formulations which are producible by the invention are suited for use as topical ointments and creams, without additional processing. The liposomes, when applied topically, can provide controlled release of a variety of topical medications, such as anti-bacterial or anti-fungal agents, and steroids, and can also serve as a source of moisturizing lipids.

For ophthalmic applications, the paste formulations would provide advantages of enhanced retention at the ocular surface, by virtue of the high viscosity of the material, and controlled drug release, by virtue of the high percentage of encapsulated drug.

The following examples illustrate various embodiments of the invention, but are in no way intended to limit the scope thereof.

EXAMPLE I

Solvent Infusion Without Liposome Extrusion

Phosphatidylcholine (PC) was obtained from Asahi Lipids (Japan), cholesterol (CH) from Sigma Chemical Co. (St. Louis, MO), and phosphatidylglycerol (PG) were obtained from Avanti Lipid (Birmingham AL).

PC (55 mole percent), cholesterol (45 mole percent) and PG (5 mole percent) were dissolved in 270 ml of Freon, to a final lipid concentration of 500 $\mu$m/ml. A 1 mM solution of carboxyfluorescene (CF) in 10 mM Tris-Hcl, pH 7.0. was prepared to a final concentration of 270 ml.

The processing system illustrated in FIG. 1 and described above in Section IA, was used for liposome preparation, except that in-line extrusion was not employed. The lipid-in-solvent solution (270 ml) was placed in the solvent feed tank and equilibrated to 4° C. by means of the circulating temperature bath. The aqueous CF solution 1270 ml) was placed in the hydration tank and equilibrated to 20° C.

The lipid solution was infused into the hydration tank at a flow rate of 2.7 ml/minute; i.e., at 1 ml/min/100 ml of aqueous medium. with the speed control mixer in the hydration tank set at about 850 revolutions/minute. The tank was maintained at negative pressure (about 200 mbar), and the solvent that boiled off was condensed and fed into a solvent recovery tank. The amount of solvent in the tank quickly reached equilibrium. At periodic intervals during the solvent infusion an aliquot of the liposome suspension in the hydration tank was drawn off for assaying (a) lipid concentration, (b) liposome size distribution, and (c) encapsulation efficiency. The suspension samples were withdrawn at times corresponding to calculated lipid concentrations, in the liposome suspension, of 50, 100, 150, 200, 250, 300, 350, and 400 $\mu$m/ml, i.e., about every 12.5 minutes duting the solvent infusion process.

The lipid concentration of the samples was determined by the method of Bartlett. Liposome sizes and size distributions were determined from electron photomicrographs. The suspensions were fixed and stained conventionally, and embedded in an epoxy block for sectioning. To determine encapsulation efficiencies the samples were pelleted by ultracentrifugation, and the liposome pellets resuspended to the pre centrifugation volume in CF-free Tris buffer. The resuspended liposomes were solubilized by the addition of 1/20 volumes of 10% Triton-X 100, and the CF concentration was determined by fluorescence emission, at an excitation wavelength of 492 nm, and an emission wavelength at 520 nm. The concentration of CF in the original aqueous medium was similarly determined, after suitable dilution with Triton-X 100. Percent encapsulation was determine from the ratio of CF in the liposome pellet/CF in the original medium.

Table 1 below shows typically results obtained from three different tests. In the first test, liposome samples were withdrawn at time points corresponding to lipid concentrations between 25 and 200 μm/ml, as shown. Actual lipid, determined from the Bartlett assay, are shown in the middle column. Encapsulation efficiencies are given in the column at the right. The consistently lower lipid concentrations relative to the expected concentrations, is presumably due to the basic volume displacement of the liposomes themselves. As seen, encapsulation efficiencies of greater than about 50% are achieved at lipid concentrations above about 150 μm/ml.

TABLE 1

| Sample (mM lipid) | Actual Lipid (mM lipid) | Encapsulation (% of total CF) |
| --- | --- | --- |
| 25 | 19.56 | 30.54 |
| 50 | 35.86 | 33.76 |
| 100 | 112.78 | 42.60 |
| 150 | 141.47 | 56.27 |
| 200 | 174.56 | 57.87 |
| 100 | 97.26 | 32.50 |
| 200 | 171.54 | 52.13 |
| 250 | 218.88 | 52.13 |
| 300 | 250.90 | 61.61 |
| 350 | 285.76 | 63.78 |
| 400 | 336.99 | 66.35 |
| 200 | 125.29 | 49.78 |
| 250 | 134.37 | 51.54 |
| 300 | 189.08 | 59.91 |
| 350 | 241.83 | 61.23 |
| 400 | 297.72 | 65.20 |

The morphologic appearance of the liposomes at sample concentrations of 50, 100, 150, and 200 μm/ml are shown in FIGS. 4A–4B. At 50 μm/ml, the liposomes are quite heterodisperse, with sizes ranging from submicron sizes to 10 microns or greater. At 100 μm/ml, the reduction of larger liposomes to more uniform sizes of about 1.5 microns or larger is seen. At 150 and 200 μm/ml, the suspension is substantially free of liposomes with sizes greater than about 1.5 microns.

A second test examined encapsulation efficiencies in the lipid concentration range 100–400 μm/ml, i.e., the highest concentration being reached by infusing all of the lipid-in-solvent solution into the aqueous medium. At the final lipid concentration, the suspension had a paste-like consistency that would make solvent infusion of further lipid material difficult. As seen, increasing the lipid concentration further enhances encapsulation efficiency up to about 66% efficiency.

A third test, shown at the bottom in Table I for lipid concentrations between 200–400 μm/ml, is consistent with the earlier test.

EXAMPLE II

Liposome Sizing After Solvent Infusion

Suspensions of liposomes containing encapsulated CF were sized by extrusion through a 0.4 micron polycarbonate membrane obtained Nucleopore Corp. Pleasanton, CA). The liposomes were extruded at an extrusion pressure of 200 psi. The highest lipid concentration which could be extruded was 350 μm/ml, and there the initial extrusion pass was quite slow. Particle sizes after extrusion were confirmed with a Nicomp Laser particle Sizer, Model 200 (Nicomp Corp., Goleta, CA) calibrated with latex particles. All of the suspensions showed particle sizes predominantly in the 0.1–0.4 micron range.

The encapsulation efficiencies of the extruded liposomes were determined as above, by pelleting the liposomes, resuspending in CF-free buffer, and comparing total CF concentration in the liposomes with that in the original aqueous suspension.

The results are shown in Table II below. A comparison of the encapsulation efficiencies before and after extrusion (Tables 1 and 2 respectively) show that substantial amounts of originally encapsulated CF is lost on extrusion. although final encapsulation efficiencies of about 40% or higher are obtained at high lipid concentrations.

TABLE 2

| Sample (mM lipid) | Actual Lipid (mM lipid) | Encapsulation (% of total CF) |
| --- | --- | --- |
| 100 | 86.48 | 22.05 |
| 200 | 160.06 | 27.25 |
| 250 | 222.66 | 29.62% |
| 300 | 195.24 | 26.06% |
| 100 | 52.88 | 9.25 |
| 200 | 110.16 | 18.50 |
| 250 | 145.63 | 29.96 |
| 300 | 168.27 | 39.65 |
| 350 | 205.23 | 44.93 |

EXAMPLE III

Liposomes with Encapsulated Calcitonin partially hydrogenated soy phosphatidylcholine PHSPC) was obtained from American Lecithin (Atlanta, Ga.); and cholesterol (CH) and α-tocopherol (α-T). from Sigma Chemical Co, (St. Louis. MO).

PHSPC (67 mole percent), cholesterol (33 mole percent) and α-T (0.1 mole percent) were dissolved in ml of "Freon 11". to a final lipid concentration of about 300 mole/ml. The aqueous medium in the system was 50 ml of a solution of $^{125}$I-labelled calcitonin (200 μg/ml) in acetate buffer (4 g/l sodium acetate), pH 4.2.

The solvent-infusion processing was carried out exactly as described in Example I, with the lipid solution being infused into the hydration tank at a flow rate of about 0.5 ml/minute i.e., 1 ml/min/100 ml of aqueous medium. The final concentration of liposomes in the suspension, at the end of the processing. was 288 μmole/ml. Aliquots of the final suspension material were diluted 1:10, 1:20, or 1:40 with drug-free buffer and vortexed to obtain a uniform dispersion of the liposomes. The total recovery of radioactive material shown for two separate preparations in Table 3 below indicates substantially 100% recovery of calcitonin material at each of the three dilutions.

The diluted samples were centrifuged at high speed to pellet the liposomes, and the radioactivity in the pellet was measured and compared with the total radioactivity contained in the sample. The ratio of the two values was used to calculate percent encapsulation of calcitonin. The results are shown in Table 3 for each of the two preparations examined. As seen, the average percent encapsulation measured for each preparation was greater than about 60%.

TABLE 3

|  | 1:10 | 1:20 | 1:40 |
|---|---|---|---|
| Preparation 1 | | | |
| Recovery (%) | 102.32 | 97.60 | 95.09 |
| Encapsulation (%) | 58.75 | 64.28 | 60.48 |
| Preparation 2 | | | |
| Recovery (%) | 97.75 | 103.46 | 92.19 |
| Encapsulation (%) | 61.65 | 59.28 | 63.12 |

The size distribution of the liposomes in the preparations was quite heterodisperse, showing a size range from about 0.1 to 10.0 microns. This result indicates the degree of liposome size heterogeneity which can be expected in the method in the absence of charged lipid components. By contrast, where charged lipid components are used, as in Example I, maximum liposome sizes of about 1.5 microns can be expected.

EXAMPLE IV

Liposomes with Enoapsulated Propranolol

PC (Example I) and $^3$H-propranolol (1-isopropylamino)-3-(1-naphthyloxy)-2-propanol) were dissolved in 50 ml of Freon 11/ethanol 10:1 (v/v) to a final lipid concentration of about 300 $\mu$mole/ml, and a final propranolol concentration of 100 mg/ml. The aqueous medium in the system was 50 ml of 10 mM Tris HCl, pH 7.0.

The solvent-infusion processing was carried out exactly as described in Example I, with the lipid solution being infused into the hydration tank at a flow rate of about 0.5 ml/minute. i.e., 1 ml/min/100 ml of aqueous medium. The final concentration of liposomes in the suspension, at the end of the processing, was 288 $\mu$mole/ml. An aliquot of the final suspension material was diluted 1:5 with buffer and vortexed to obtain a uniform dispersion of the liposomes. The diluted sample was centrifuged at high speed to pellet the liposomes, and the total radioactivity in the pellet was measured and compared with the total radioactivity contained in the sample. The ratio of the encapsulated to total material was about 75%.

EXAMPLE V

Integrated Solvent Infusion/Liposome Extrusion

Suspensions of liposomes were prepared as in example I, with the following two modifications: (1) The lipid-in-solvent solution contained 500 $\mu$m/ml, and (2) the aqueous liposome suspension in the hydration tank was circulated through the filter extrusion line in the system shown in FIG. 2. This line includes a high-pressure pump and a sealed membrane chamber which here was equipped with a 0.4 micron polycarbonate filter. The pressure on the upstream side of the filter chamber was maintained at about 250 psi, giving a flow rate, at the initial stages of operation, of about 30–50 ml/minute.

In contrast to the solvent infusion technique without integrated sizing, the liposome suspension was sufficiently fluid even at the highest lipid concentration (about 500 $\mu$m/ml) to allow continued infusion. The method also a lowed for extrusion of a more concentrated lipid suspension. i.e., 500 $\mu$m/ml vs 350 $\mu$m/ml. when the extrusion is carried out following liposome preparation by solvent infusion.

The encapsulation efficiencies of the liposome material at various concentrations is shown in Table 4. The data show that concentrated formulations having (a) sizes less than about 0.4 microns, and (b) encapsulation eficiencies above 50% can be made directly by the method.

TABLE 4

| Sample (mM lipid) | Actual Lipid (mM lipid) | Encapsulation (% of total CF) |
|---|---|---|
| 100 | 57.92 | 17.62 |
| 200 | 101.42 | 18.06 |
| 250 | 156.52 | 20.26 |
| 300 | 171.85 | 24.67 |
| 350 | 210.06 | 31.72 |
| 400 | 332.82 | 49.34 |
| 500 | 399.55 | 55.95 |

While the invention has been described and illustrated with respect with preferred embodiments, it will be apparent to one skilled in the art that various changes and modifications can be made without departing from the invention.

It is claimed:

1. A method of preparing a suspension of liposomes having a lipid concentration of greater than about 300 $\mu$m/ml, and liposomes sizes no greater than about 0.4 microns, said method comprising
    dissolving liposomes-forming lipids in a chlorofluorocarbon solvent, to form a lipid-in-solvent solution,
    injecting the lipid solution, in liquid form, into an aqueous medium, under pressure and temperature conditions at which lipid frothing is largely prevented, and at an injection rate that produces predominantly oligolamellar liposomes,
    during said injecting, removing injected chlorofluorocarbon solvent from the aqueous medium at substantially the same rate that it is introduced into the medium,
    also during said injecting, extruding liposomes formed in the aqueous medium to reduce the sizes of the largest liposomes to less than about 0.4 microns, and
    continuing said injecting, removing and extruding until the lipid concentration in the aqueous medium is at least about 300 $\mu$m/ml.

2. The methopd of claim 1, wherein said lipids are dissolved in "Freon 11", at a concentration of between about 100–700 $\mu$m/ml.

3. The method of claim 2, wherein the lipid solvent also includes "Freon 21".

4. The method of claim 1, wherein the lipid solution has a lipid concentration of between about 250–700 $\mu$m/ml, and the lipid solution is injected into the aqueous medium, at an injection rate of about 0.5–2 ml lipid solution per 100 ml aqueous medium per minute.

5. The method of claim 1, wherein the liposomes are extruded through a polycarbonate membrane having a selected pore size of between 0.1–0.4 microns.

6. The method of claim 1, wherein the liposomes are extruded through an asymmetric ceramic filter having a pore size of about 1 micron.

7. The method of claim 1, for use in producing liposomes containing an entrapped lipophilic compound, wherein the compound is dissolved in the lipid solution.

8. The method of claim 7, wherein the compound is selected from the group consisting of protaglandins, amphotericin B, progesterone, isosorbide dinitrixe, testosterone, nitroglycerin, estradiol, cortisone, dexamethasome and related esters, and betamethasone valerate.

9. The method of claim 1, for use in preparing liposomes containing an encapsulated water-soluble compound selected from the group consisting of calcitonin, atriopeptin, $\alpha$-1 antitrypsin, interferon, oxytocin, vasopressin, insulin, interleukin-2, superoxide dismutase tissue plasminogen activator plasma factor 8, epidermal growth factor, tumor necrosis factor. lung surfactant protein, and lipocortin, wherein the compound is originally dissolved in the aqueous medium.

10. The method of claim 9, wherein the final concentration of lipids in the suspension is between about 400–600 $\mu$mole/ml, and at least about 50% of the compound is in liposome-encapsulated form.

11. The method of claim 1 for use in preparing liposomes containing a water-soluble compound which is soluble in a chlorofluorocarbon solvent also containing a solvent which is co-miscible with water and chlorofluorocatbon. wherein the compound is originally dissolved in the lipid solvent.

12. The method of claim 11, wherein the compound is propranolol, and the chlorofluorocarbon solvent contains a volume percentage of ethanol needed to solubilize the compound in the solvent.

13. The method of claim 1, for use in forming liposomes which are predominantly free of liposomes less than about 0.1 micron in size, wherein the suspension is formed in a reactor which is being fed continuously with both lipid solution and aqueous medium and which further includes subjecting the suspension to diaf-iltration during said infusing, to form a filtrate containing liposomes which are predominantly less than about 0.1 microns in size, nd a retentate containing liposomes predominantly above about 0.1 microns in size, and in using the lipid solution into the filtrate.

14. The method of claim 1, which further includes sterilizing the liposome injection by filtration through a sterilization filter.

* * * * *